United States Patent
McCormack et al.

(10) Patent No.: US 6,719,742 B1
(45) Date of Patent: Apr. 13, 2004

(54) PATTERN EMBOSSED MULTILAYER MICROPOROUS FILMS

(75) Inventors: Ann Louise McCormack, Cumming, GA (US); Joy Francine Jordan, Marietta, GA (US); William Bela Haffner, Ballground, GA (US); Mark John Beitz, Appleton, WI (US); Hong Y. Lin, Sacramento, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/469,094

(22) Filed: Dec. 21, 1999

Related U.S. Application Data

(60) Provisional application No. 60/114,283, filed on Dec. 30, 1998.

(51) Int. Cl.[7] .............................. A61F 13/50; A61F 13/20
(52) U.S. Cl. .................. 604/385.01; 604/367; 604/380
(58) Field of Search .............................. 604/358, 367, 604/383, 384, 378–380; 428/131, 138

(56) References Cited

U.S. PATENT DOCUMENTS

| | | | |
|---|---|---|---|
| 3,379,560 A | 4/1968 | Tharp | 117/121 |
| 3,675,654 A | 7/1972 | Baker et al. | 128/287 |
| 3,952,746 A | 4/1976 | Summers | 128/287 |
| 4,113,911 A | 9/1978 | LaFitte et al. | 428/284 |
| 4,196,245 A | 4/1980 | Kitson et al. | 428/198 |
| 4,231,370 A | 11/1980 | Mroz et al. | 128/287 |
| 4,237,889 A | 12/1980 | Gobran | 128/287 |
| 4,333,465 A | 6/1982 | Wiegner | 128/290 |
| 4,436,520 A | 3/1984 | Lipko et al. | 604/385 |
| 4,623,340 A | 11/1986 | Luceri | 604/395 |
| 4,662,875 A | 5/1987 | Hirotsu et al. | 604/389 |
| 4,662,876 A | 5/1987 | Wiegner | 604/380 |
| 4,801,494 A | 1/1989 | Datta et al. | 428/283 |
| 5,006,394 A | 4/1991 | Baird | 428/138 |
| 5,133,707 A | 7/1992 | Rogers et al. | 604/389 |
| 5,147,346 A | 9/1992 | Cancio et al. | 604/389 |
| 5,169,712 A | 12/1992 | Tapp | 428/315.5 |
| 5,182,069 A | 1/1993 | Wick | 264/210.2 |
| 5,192,606 A | 3/1993 | Proxmire et al. | 428/284 |
| 5,261,899 A | 11/1993 | Visscher et al. | 604/367 |
| 5,364,381 A | 11/1994 | Soga et al. | 604/366 |
| 5,389,093 A | 2/1995 | Howell | 604/361 |
| 5,431,643 A | 7/1995 | Ouellette et al. | 604/385.1 |
| 5,510,161 A | 4/1996 | Lloyd | 428/40 |
| 5,571,586 A | 11/1996 | Gobran | 428/41.3 |
| 5,575,782 A | 11/1996 | Hasse et al. | 604/385.1 |
| 5,629,063 A | 5/1997 | Gobran | 428/40.1 |
| 5,897,541 A | 4/1999 | Uitenbroek et al. | 605/358 |
| 6,075,179 A * | 6/2000 | McCormack et al. | |
| 6,277,479 B1 * | 8/2001 | Campbell et al. | |
| 6,309,736 B1 * | 10/2001 | McCormack et al. | |

FOREIGN PATENT DOCUMENTS

| | | |
|---|---|---|
| EP | 0259128 | 1/1992 |
| GB | 1070514 | 6/1967 |
| GB | 1265483 | 3/1972 |
| GB | 2255745 | 11/1992 |
| JP | 08019570 | 1/1996 |
| WO | 94/28846 | 12/1994 |
| WO | 96/10380 | 4/1996 |
| WO | 98/05502 | 2/1998 |
| WO | 99/32272 | 7/1999 |

* cited by examiner

*Primary Examiner*—Weilun Lo
*Assistant Examiner*—Michele Kidwell
(74) *Attorney, Agent, or Firm*—Steven D. Flack

(57) ABSTRACT

Pattern embossed low gauge films are disclosed having multiple microporous film layers with distinct coloration, such as a dark colored layer and a light colored layer, wherein the color of the underlying film causes a visible color contrast only at the embossed regions and yet does not discolor the outer most layer. Also disclosed are film laminates and personal care articles incorporating such multilayer films.

23 Claims, 3 Drawing Sheets

PATTERN EMBOSSED MULTILAYER MICROPOROUS FILMS

This application claims priority from U.S. Provisional Application No. 60/114,283 filed on Dec. 30, 1998.

FIELD OF THE INVENTION

The present invention relates to microporous films and, more particularly, relates to patterned embossed multilayered films and methods of making the same.

BACKGROUND OF THE INVENTION

Absorbent articles, for example personal care products, generally comprise an absorbent material for absorbing and retaining liquids and a liquid impervious outer cover. Various films have been used heretofore within the outer cover to provide a liquid barrier and prevent leakage of liquids from the absorbent material. These films have employed various pigments or opacifying fillers in order to provide an opaque film that masks the interior of the article. Examples of such opaque films are described in U.S. Pat. No. 5,006,394 to Baird and U.S. Pat. No. 5,261,899 to Visscher et al. In addition, outer covers for personal care articles have also utilized embossed multilayer structures to provide a film having multi-colored patterns therein. As an example, U.S. Pat. No. 5,897,541 to Uitenbroek et al. describes a multilayer structure comprising a first layer having opaque areas and transparent areas and a second layer of a colored material wherein the color of the second layer shows through the transparent areas of the first layer. In one embodiment, the first layer can comprise an opaque microporous film having transparent areas, formed therein by the application of heat and/or pressure, wherein the color of an underlying layer shows through the parent areas, In addition, UK Patent No. 1,070,514 teaches a white, substantially opaque polybutylene film which can be rendered substantially transparent in areas subjected to heat or pressure. Color can show through the transparent areas when the polybutylene film is laminated to a colored substrate. In a similar aspect, U.S. Pat. No. 4,623,340 to Luceri teaches a body-side layer for an absorbent product comprising an outer light colored liquid-pervious, opaque sheet, such as a nonwoven web or perforated film, and an inner dark colored sheet. The two layers are co-embossed to form depressed areas and undepressed areas wherein the depressed areas color contrast with the light- colored undepressed areas.

However, highly breathable microporous films are often extremely thin films that provide reduced opacity characteristics. Thus, the ability to provide the desired color contrast through embossed multilayer structures is diminished since the color of an underlying dark layer will show through thin microporous film resulting in limited or poor color contrast. Further, the ability of such films to adequately mask and/or neutralize colors within the interior of personal care articles has also proven difficult to achieve.

SUMMARY OF THE INVENTION

The aforesaid needs are fulfilled and the problems experienced by those skilled in the art overcome by multilayer films of the present invention comprising: (i) a first microporous layer having a thickness less than about 30 micrometers and comprising polymer and at least 35%, by weight, filler; and (ii) a second microporous layer substantially continuously joined to the first layer and having a thickness less than about 30 micrometers, the second microporous layer comprising polymer, coloring agent and at least 35%, by weight, filler. The multilayer films have a total basis weight less than about 45 g/m$^2$, a WVTR in excess of 500 g/m$^2$/24 hours and a hydrohead of at least 50 mbars. Additionally, the multilayer films have embossed and non-embossed regions wherein the embossed regions color-contrast with said non-embossed regions. Desirably, the second layer is darker than the first layer and the embossed regions of the first layer are translucent. The embossed regions of the second layer can be translucent or opaque. In a further aspect, the second layer can comprise a multi-toned film wherein the color within the embossed regions is darker than that within the non-embossed regions and/or has a more intense color than that within the non-embossed regions. Further, the non-embossed regions of the second layer desirably have a Hunter Color Number L* above 70. The multilayer film can further comprise addition microporous layers as desired. The multilayer films of the present invention can also be used to form multilayer laminates such as, for example, nonwoven/film laminates. The multilayer films and laminates thereof have numerous applications and are particularly well suited for use as or within a liquid impervious outer cover for personal care articles.

DEFINITIONS

As used herein, the term "comprising" is inclusive or open-ended and does not exclude additional unrecited elements, compositional components, or method steps.

As used herein the term "nonwoven" fabric or web means a web having a structure of individual fibers or threads which are interlaid, but not in an identifiable manner as in a knitted or woven fabric. Nonwoven fabrics or webs can be formed by many processes including, but not limited to, meltblowing processes, spunbonding processes, hydroentangling, air-laid and bonded-carded web processes.

As used herein, the term "machine direction" or MD means the direction of the fabric in the direction in which it is produced. The term "cross machine direction" or CD means the direction of the fabric substantially perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, the term "barrier" or "liquid barrier" means a film, laminate or other fabric which is relatively impermeable to the transmission of liquids and which has a hydrohead of at least about 50 mbar. Hydrohead is a measure of the liquid barrier properties of a fabric measured in millibars (mbar) as described herein below.

As used herein, the term "breathability" refers to the water vapor transmission rate (WVTR) of an area of fabric which is measured in grams of water per square meter per day ($g/m^2/24$ hours). The WVTR of a fabric, in one aspect, gives an indication of how comfortable a fabric would be to wear. WVTR can be measured as indicated below.

As used herein, the term "garment" means any type of non-medically oriented apparel that may be worn. This includes industrial workwear and coveralls, undergarments, pants, shirts, jackets, gloves, socks, and so forth.

As used herein, the term "infection control product" means medically oriented items such as surgical gowns and drapes, face masks, head coverings, shoe or foot coverings, wound dressings, bandages, sterilization wraps, wipers, lab coats, patient bedding, stretcher and bassinet sheets, and so forth.

As used herein, the term "personal care product" means personal hygiene oriented items such as diapers, training pants, absorbent underpants, adult incontinence products, feminine hygiene products, and so forth.

As used herein, the term "protective cover" means a cover for articles such as vehicles, furniture, yard and garden equipment, etc., as well as floor coverings, tents, tarpaulins, and so forth.

DESCRIPTION OF THE INVENTION

Figure 1:
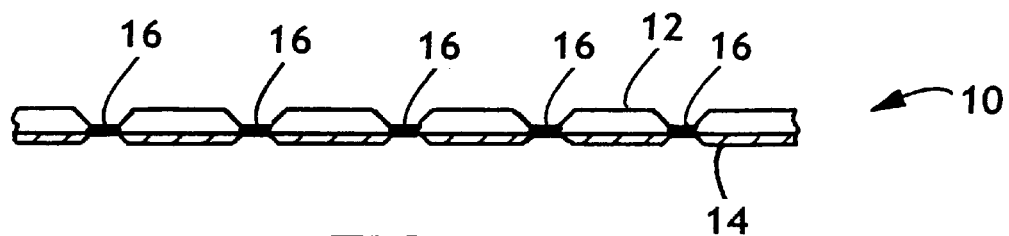
FIG. 1 is a cross-sectional view of a multilayer film of the present invention.

In one aspect and in reference to FIG. 1, the present invention is directed to a breathable multilayer film 10 comprising an upper or first microporous film layer 12 and second microporous film layer 14 adjacent one another and having embossed regions 16 therein. The second microporous film layer 14 has a different color, relative to that of first microporous film layer 12, wherein embossed regions 16 contrast with the color of the first microporous film 12. Embossing multilayer film 10 creates a substantially translucent region 16 which, despite being translucent, color-contrasts with the first microporous film layer 12. As a particular example, first microporous film layer 12 can be white and second microporous film can be, for example, purple wherein embossed regions color-contrast with the white appearance of the first microporous film having a purple color or hue. The breathable microporous film 10 can optionally have a sheet (not shown), such as a nonwoven web, laminated thereto.

The first and second microporous films can each comprise microporous breathable films wherein the multilayer film has a WVTR greater than 500 $g/m^2/day$, and more desirably wherein the multilayer film has a WVTR in excess of about 1000 $g/m^2/day$ and still more desirably wherein the multilayer film has a WVTR in excess of about 3500 $g/m^2/day$.

Additionally, the multilayer films should collectively comprises a liquid barrier having a hydrohead of at least about 50 mbar and desirably the, multilayers and/or laminates of the present invention have hydrohead values greater than about 80 mbar and still more desirably greater than about 150 mbar. In addition, the first microporous film layer can have a thickness of between about 2 $\mu m$ (micrometers) and about 30 $\mu m$ and still more desirably between about 5 $\mu m$ and about 15 $\mu m$. As used herein 'film thickness' is with reference to the non-embossed regions of the film. Further, the first microporous film can have a basis weight of at least 2 $g/m^2$ and more desirably has a basis weight between about 5 $g/m^2$ and about 15 $g/m^2$. The breathable films can be formed by any one of various methods known in the art. Desirably the first breathable film layer comprises a stretched filled-film that includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. Preferably the first breathable microporous film layer and the second microporous film layer are simultaneously made such as, for example, by co-extrusion. As an example, methods of forming multilayer films are disclosed in U.S. Pat. No. 4,522,203; U.S. Pat. No. 4,734,324 and commonly assigned U.S. patent application Ser. No. 08/724,435 to McCormack et al. and U.S. patent application Ser. No. 08/929,562 to Haffner et al.; the entire contents of which are incorporated herein by reference.

While a variety of microporous films are known in the art and believed suitable for use with the present invention, an exemplary breathable film comprises a stretched microporous filled-film. Such films are typically filled with particles or other matter and then crushed or stretched to form a fine pore network throughout the film. The fine pore network allows gas and water vapor to pass through the film while acting as a barrier to liquids and particulate matter. The amount of filler within the film and the degree of stretching are controlled so as to create a network of micropores of a size and frequency to impart the desired level of breathability to the fabric. By way of example only, exemplary microporous films are described in U.S. Pat. No. 5,855,999 to McCormack et al.; U.S. Pat. No. 5,695,868 to McCormack; U.S. Pat. No. 5,800,758 to Topolkaraev et al.; U.S. patent application Ser. No. 08/724,435 to McCormack et al.; U.S. patent application Ser. No. 09/122,326 to Shawver et al.; U.S. Pat. No. 4,777,073 to Sheth; and U.S. Pat. No. 4,867,881 to Kinzer; the entire contents of the aforesaid references are incorporated herein by reference.

Thermoplastic polymers suitable for use in the fabrication of films of the present invention include, but are not limited to, polyolefins including homopolymers, copolymers, terpolymers and blends thereof. In this regard, amorphous polyolefin and/or "polyolefin based" films are also believed suitable for use in the present invention. For purposes of the present invention a polymer is considered to be "polyolefin-based" if olefin polymers comprise greater than 50 weight percent of the polymerc portion of the film, exclusive of any filler materials. Additional film forming polymers which may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyester, polyethylene terephthalate (PET), nylon, ethylene vinyl alcohol (EVOH), polystyrene (PS), polyurethane (PU), polybutylene (PB), and polybutylene terephthalate (PBT). However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends.

As indicated above, breathable stretched filled-films can include filler to impart microporosity to the film upon stretching. As used herein a "filler" is meant to include particulate and/or other forms of materials which can be added to the film polymer extrusion blend which will not chemically interfere with or adversely affect the extruded film and further which can be substantially uniformly dispersed throughout the film. Generally the fillers will be in particulate form with average particle sizes in the range of about 0.1 to about 10 microns, and desirably from about 0.1 to about 4 microns. As used herein the term "particle size" describes the largest dimension or length of the filler. Both organic and inorganic fillers are contemplated for use with the present invention provided they do not interfere with the film forming process and subsequent embossing or laminating processes. Examples of fillers include, but are not limited to, calcium carbonate ($CaCO_3$), various clays, silica ($SiO_2$), alumina, barium sulfate, talc, sodium bicarbonate, magnesium sulfate, zeolites, aluminum sulfate, cellulose-type powders, diatomaceous earth, gypsum, magnesium sulfate, magnesium carbonate, barium carbonate, kaolin, mica, carbon, magnesium oxide, aluminum hydroxide, pulp powder, wood powder, cellulose derivatives, polymeric particles, chitin and chitin derivatives and the like. The filler particles may optionally be coated with a fatty acid, such as stearic acid or behenic acid, and/or other material in order to facilitate the free flow of the particles (in bulk) and their ease of dispersion into the polymer. The microporous filled-films desirably comprise from about 20% to about 40% filler by volume and more desirably comprise between about 30% and about 40% filler by volume. As a particular example, a filled-film using a calcium carbonate particles, or a filler with a similar density to that of calcium carbonate, desirably contains at least about 35% by weight filler (based upon the total weight of the filled-film), and more desirably from about 45% to about 70% by weight filler.

Films that have been stretched to create a network of micropores, thereby rendering the film breathable, are typically stretched to the point of "stress-whitening". Thus, since the network of micropores created by the separation of the polymeric matrix from the filler particles creates a white, opaque film, the use of such fillers alone can impart a white appearance to the film. Optionally, coloring agents such as dyes and/or pigments can be used in addition to filler to create breathable microporous films having a variety of colors. Suitable coloring agents include both organic and/or inorganic pigments and dyes. Desirably the coloring agents are used in amount less than about 2.0% by weight (based upon the polymeric portion of the film), and even more desirably between about 0.01% and about 0.5% by weight (based upon the polymeric portion of the film). Pigments and/or dyes can be added to the film by means known in the art. In this regard, pigments are desirably added by pre-compounding the pigment with the desired resin to form a resin concentrate with a relatively high percent of pigment and then blending a selected amount of the resin concentrate with unpigmented resin during processing to form a matrix having the desired pigmentation levels. Opacifying agents, an example being titanium dioxide, can optionally be used in the first layer in addition to the filler. Desirably the opacifying agents are present in an amount from about 0% up to about 10% by weight (based on the total weight of the filled-film).

In addition, each of the microporous films discussed herein can optionally include one or more additional materials or additives as is known in the art such as, for example, UV stabilizers, antioxidants, thermal stabilizers, tackifiers, anti-blocking agents, optical brighteners, compatibilizers, processing aids and the so forth.

The second breathable microporous film layer can comprise a film similar in form and composition to those described above with regard to the first microporous film. Desirably, the first microporous film layer and the second microporous film layer are substantially continuously joined to one another. In a preferred embodiment of the present invention the first and second microporous films are co-extruded to form a cohesive structure. The desired color of the second microporous film layer can likewise be achieved using one or more coloring agents. The second microporous film has a color or shade which has a different Hunter Color Number than that of the first layer. Desirably, the second microporous film is a color and/or shade sufficiently distinct from the first microporous film such that (i) the embossed regions sufficiently contrast with the non-embossed regions such that the L* numbers (light-to-dark scale) vary by at least 5 units, and desirably vary by at least about 7.5 units and still more desirably vary by at least about 10 units; and/or (ii) the a* and/or b* units (chroma differences) contrast by at least 1.0 unit, desirably by at least about 2.0 units and still more desirably by at least about 3.0 units.

For thin films such as those of the present invention, it can be difficult to provide an upper layer wherein the darker color of the second or underlying microporous film does not show through the first microporous film layer. This problem can be particularly pronounced when using a thin white or lighter colored film since the underlying darker film can adulterate or darken the true color of the thin overlying film. In this regard it has been found that the color of filled-films becomes lighter upon stretching due to the network of micropores formed within the film. However, the embossed regions of the colored microporous film exhibit intensified color and, thus, the colored microporous film itself has relatively darker and lighter regions. Thus, the films of the present invention allow for thin films with good color-contrast in the embossed regions without requiring a deeply colored film that substantially darkens or adulterates the lighter color of adjacent layers. Accordingly, when a first layer is desired having a light appearance (e.g. white, off-white and so forth) it is desirable that the underlying second colored layer have an L* number not less than about 70 and still more desirably an L* number not less than about 85. This color problem can be further improved by employing a more opaque top sheet, a brighter top sheet, an opaque or dark backing layer that has a low light reflectance and/or a first layer containing optical brighteners. In addition, improved color contrast between the embossed regions and the first film layer can be achieved by including opacifying agents within the colored second layer. Desirably the second layer has less than about 10% by weight (based upon the total weight of the filled-film) $TiO_2$ and more desirably has between about 0.5% and about 5% by weight $TiO_2$.

By way of examples, specific combinations of the first and second microporous films can comprise: white/blue; white/green; white/yellow; white/purple; white/red; pink/purple; blue/red; yellow/blue; and so forth. The second film desirably has pigments and/or dyes in amounts less than about 2%, by weight (based upon the polymeric portion of the film), and still more desirably between about 0.01% by weight and about 0.5% by weight. Either the first or second layers can comprise the dark layer depending on the desired appearance of the article incorporating the multilayer film.

The microporous films can be embossed using heat and/or pressure to create compressed, translucent regions that contrast with the color or shade of the non-embossed regions of the first microporous film. The color contrast is provided by the distinct color or shade of the embossed regions. In this regard, the first and second layers within the embossed regions become substantially non-porous and thereby reducing the light-scattering effect of the microporous film and allowing the color or hue of the underlying second microporous film to be visible. The embossed regions can be imparted by one or more methods suitable for permanently embossing thin films. By way of example only, the compressed regions can be formed using heat and/or pressure as well as other methods such as ultrasonic energy and so forth. As a particular example, compression of selected regions of the microporous films can be achieved via the use of patterned roller assemblies such as are commonly used in point bonding processes. Point bonding generally refers to the process of mechanically compressing one or more layers at numerous small, discrete points. Desirably the layes are embossed by thermal point bonding which generally involves passing one or more layers to be bonded between heated rolls such as, for example, an engraved or patterned roll and a second roll. The engraved roll is patterned in some way so that the fabric is not bonded over its entire surface, and the second roll can either be flat or patterned. Various patterns for engraved or patterned rolls have been developed for functional as well as aesthetic reasons and, by way of example only, various bond patterns are described in U.S. Pat. No. 3,855,046 to Hansen et al.; U.S. Pat. No. 4,374,888 to Bomslaeger; U.S. Pat. No. 5,635,134 to Bourne et al.; U.S. Pat. No. 5,620,779 to Levy et al.; U.S. Pat. No. 5,714,107 to Levy et al.; U.S. Design Pat. No. 390,798 to Brown; U.S. Pat. No. 5,858,519 to Stokes et al.; and U.S. Design Pat. No. 369,907 to Sayovitz et al. An exemplary bond pattern is a 'Baby Objects' bond pattern wherein the raised surface is designed to create a repeating pattern of bonded regions representative of various identifiable objects, and such a pattern is described in U.S. Design Pat. No. 356,688 to Uitenbroek et al., the entire contents of which is incorporated herein by reference.

Figure 6:
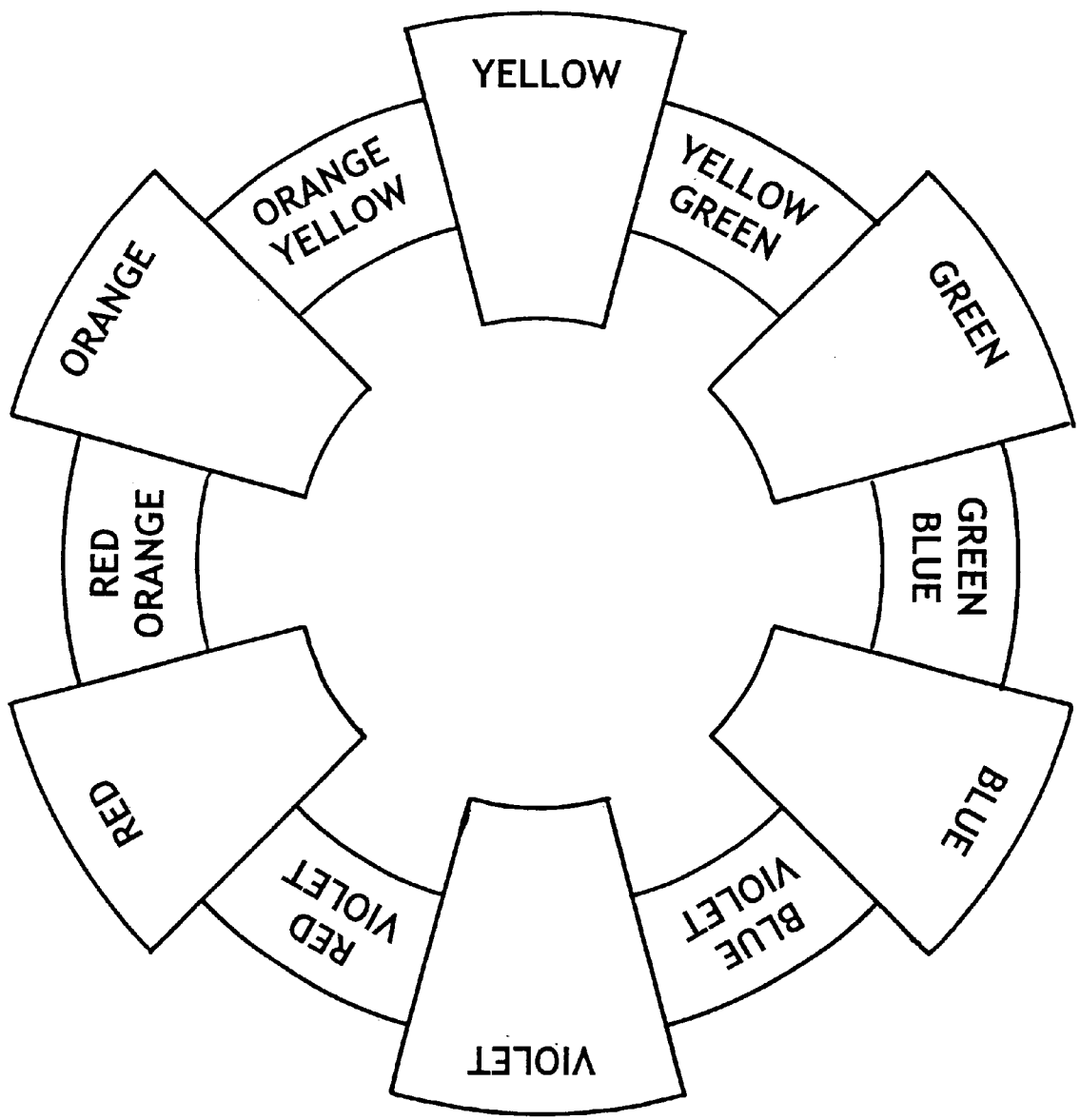
FIG. 6 is a color wheel.

In a further aspect of the invention and with regard to color selection, masking of the inner portions of an absorbent article can be improved by employing colors that in effect neutralize the colors within the interior of the article. In this regard, when colors are mixed they actually function by each independently absorbing light and thus the resulting color shade is achieved as a result of the "subtractive mixing" of the multiple colors. Accordingly, mixing certain colors can give the appearance of a distinct color or shade whereas the effect of mixing three primary colors, when sufficiently concentrated, is to absorb all the light and a produce black, i.e. the absence of color. Therefore, while the absorbent cores of diapers take on a yellowish color after absorbing urine, by utilizing a purple or violet colored film in the multilayer film the combination of these colors yields a light gray shade. However, when utilizing a blue colored film in the multilayer film the combination yields a green color. Therefore, selecting a film color that maximizes the subtractive mixing effect of the colors also maximizes the film's ability to neutralize the underlying color. The specific color to be neutralized will often vary with respect to the product and the neutralizing colors best suited to a given product can be selected by choosing a color, from a color wheel as shown in FIG. 6, that is opposite or substantially opposite the color to be neutralized.

In a further aspect, the breathable microporous films can optionally be laminated to an additional layer or sheet. Often it will be desirable to laminate the films to a sheet material whereby the laminate takes advantage of the strength and integrity of the sheet material and the barrier properties of the microporous film. The sheet material can comprise a nonwoven web, a foam, a scrim, a woven or knitted fabric and multilayer laminates thereof. When the sheet comprises the outer layer of the laminate or an article incorporating the laminate, desirably the outer sheet is not opaque and is at least substantially translucent and even more desirably diaphanous. If the outer sheet is opaque, then it must be capable of becoming at least substantially translucent upon embossing. In a preferred embodiment, the sheet can comprise a low basis weight nonwoven fabric having numerous openings or voids extending through the thickness of the fabric. As an example, the nonwoven fabric can comprise a nonwoven web of spunbond fibers having a basis weight between about 8 g/m$^2$ and about 50 g/m$^2$ and even more desirably a spunbond fiber web having a basis weight between about 12 g/m$^2$ and about 34 g/m$^2$. Spunbond fiber fabrics and methods for making the same are known in the art and, as examples, spunbond fiber fabrics and processes of making the same are described in U.S. Pat. No. 4,692,618 to Dorschner et al., U.S. Pat. No. 4,340,563 to Appel et al. and U.S. Pat. No. 3,802,817 to Matsuki et al.; and U.S. Pat. No. 5,382,400 to Pike et al. and PCT Publication No. WO98/23804; the entire content of the aforesaid references are incorporated herein by reference. Generally, methods for making spunbond fiber nonwoven webs include extruding molten thermoplastic polymer through spinnerets and drawing the extruded polymer into fibers, reducing the fiber diameter, and forming a web of randomly arrayed fibers on a collecting surface. Spunbond fiber webs can be made from various polymers and, in a preferred embodiment, the spunbond fibers desirably comprise a polyolefin and still more desirably comprise a propylene polymer. In addition, the nonwoven fabric can optionally include opacifying or coloring agents such as, for example, titanium dioxide which produces a more opaque fiber.

Figure 2:
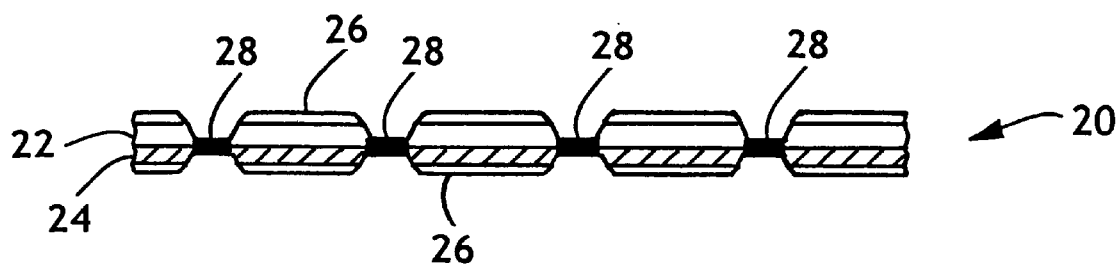
FIG. 2 is a cross-sectional view of a multilayer film of the present invention.

In a further aspect of the present invention and in reference to FIG. 2, a breathable multilayer film 20 can have two outer skin layers 26 and a first microporous film layer 22 and a second microporous film layer 24. The skin layers 26 desirably collectively comprise less than about 15% of the total film thickness and even more desirably comprise less than about 10% of the total film thickness. The skin layers can be filled or unfilled polymeric films. Desirably the second microporous film 24 is a different color, relative to the first microporous film 22, and comprises less than about 90% of the overall film thickness and more desirably comprises between about 10% and about 50% of the overall film thickness. The first microporous film can comprise between about 10% and about 90% of the overall film thickness and, with a two-layer film more desirably comprises between about 50% and about 90% of the overall film thickness. The basis weight of the entire multilayer film is desirably less than about 45 g/m$^2$ and more desirably between about 10 g/m$^2$ and about 35 g/m$^2$. As indicated above, the first and second microporous film layers and skin layers are desirably co-extruded to form a unitary multilayer film. Embossing provides the multilayer film 20 with color-contrast between the non-embossed regions of microporous film 22 and compressed regions 28 since the compressed regions become translucent and non-microporous and al he distinct color of the underlying second microporous film layer 24 to become visible.

However, due to the low basis weight of the multilayer film and the individual layers, the thickness of the overall film will typically be less than about 35 micrometers. Thus, the outer film has reduced opacity as a result of its limited thickness. In this regard it has been found that good color contrast can still be provided when using a dark underlying layer by utilizing a thin microporous film as the underlying colored layer since it is possible to provide a film which is lighter or that has a "paler" color in the unembossed regions than in the embossed region. In other words, the embossed regions within the underlying film have a darker and/or intensified color relative to the unembossed regions. This allows for a thin outer light colored film wherein the color of the inner or underlying film does not overwhelm or degrade the color of the outer layer.

In a further aspect of the present invention, it may be desirable to further increase the color-contrast between the embossed and unembossed regions of the multilayer film. Color-contrast can be improved by providing a multilayer film wherein the underlying colored layer is substantially opaque. Moreover, when incorporating a multilayer film into a personal care article, often it is desirable that the outer cover or baffle not be transparent so as to mask soiled interior absorbent layers. Thus, by adding opacifying agents to the underlying colored second layer, it is possible to provide an embossed multilayer film having good color contrast yet avoiding embossed regions which are too transparent or translucent such that soiled absorbent layers are not sufficiently masked.

Figure 3:
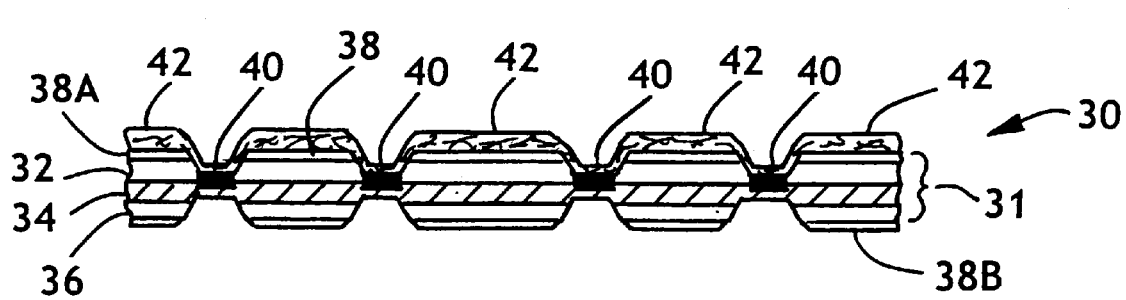
FIG. 3 is a cross-sectional view of a multilayer film laminate of the present invention.

In still a further aspect and in reference to FIG. 3, multilayer film laminate 30 is provided comprising a multilayer film 31 comprising outer thin skin layers 38 and first, second and third interior layers 32, 34, 36. The skin layers 38 desirably comprise unfilled polymeric layers and comprise a minor percent of the total film thickness whereas interior layers 32, 34 and 36 desirably each comprise microporous layers. First interior layer 32 is positioned between outer skin layer 38A and the second interior or colored layer 34. The first interior layer 32 desirably has a color lighter than that of second layer 34. In a preferred embodiment the first interior layer is white. The first interior layer can have a thickness of between about 3 $\mu$m and about 30$\mu$m and more desirably between about 5 $\mu$m and about 15 $\mu$m. The second and third layers can have a thickness similar to that of the first layer. Desirably, the total thickness of the multilayer film is between about 12 $\mu$m and about 35 $\mu$m and more desirably between about 15 $\mu$m and about 25 $\mu$m. As an example, the first interior layer 32 can comprise a stress-whitened microporous film wherein the filler and micropores provide a film having a substantially white appearance. The first interior layer 32 can comprise a filler such as, for example, from 40% to about 70% by weight calcium carbonate to impart porosity to the film. Sheet 42 can be attached to microporous film to provide additional integrity, improved hand, aesthetics and/or other characteristics as desired. Sheet 42 can comprise an opaque polymeric sheet capable of becoming translucent upon embossing such as, for example, a high basis weight and/or high coverage polyolefin nonwoven web. In a preferred embodiment the outer sheet 42 can comprise a diaphanous sheet such as a low basis weight nonwoven web. Desirably, sheet 42 comprises a polyolefin spunbond fiber web having a basis weight less than about 34 g/m$^2$. The multilayer film laminate 30 has embossed regions 40 which are non-porous and translucent so as to allow the color or hue of colored film 34 to be visually perceptible and create a more distinct patterned fabric. The embossed regions 40 can color-contrast with the non-embossed regions of the laminate 30 to create a laminate with a colored pattern therein. It is noted that second interior film layer 34 and/or third interior film layer 36 can themselves be translucent or opaque within the embossed regions 40. Desirably, however, at least one of second interior film layer 34 or third interior film layer 36 remain substantially opaque within the embossed regions 40.

The third interior layer 36 is positioned between outer skin layer 38B and the second interior layer 34. The third interior layer 36 can comprise a translucent or opaque film and desirably comprises a microporous opaque stretched filled-film such as those described herein above. Additional opacifying fillers, an example being titanium dioxide, can also be included within the third interior film 36. As a specific example, third interior film 36 can comprise from about 40% to about 65% by weight calcium carbonate and from 0 to about 10% by weight titanium dioxide (by total weight of the filled-film). By providing a third interior film with titanium dioxide the opacity is increased and it is possible to reduce the transparency of the embossed regions of the multilayer film and thereby mask the interior of the article. In addition, by providing an opaque third intermediate film it is possible to provide a distinct pattern in one side of the film and a less distinguishable or substantially indistinguishable pattern in the opposite side. Thus, when placed within a personal care article, the embossing pattern and/or hue of the second colored layer does not appear on the inside of the article. The two-sidededness can be further enhanced by employing a soft roll in combination with a hard patterned roll such as, for example, a rubber coated roll and a patterned steel roll. By feeding the multilayer film or laminate through such embossing rolls it is possible to achieve a less distinct pattern on the side of the film facing the relatively soft roll (e.g. the rubber coated roll).

Figure 4:
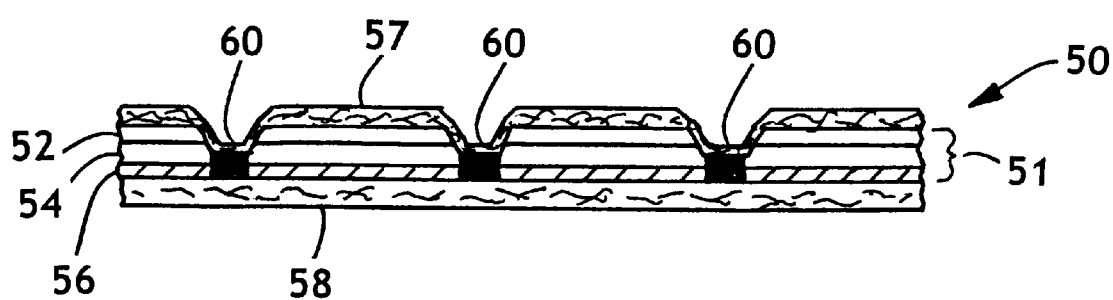
FIG. 4 is a cross-sectional view of a multilayer film laminate of the present invention.

In a further aspect and in reference to FIG. 4, multilayer laminate 50 can comprise a multilayer film 51 and a first sheet 57 attached to one side of the multilayer film 51 and a second sheet adjacent the opposite side of the multilayer film 51. Multilayer film 51 can comprise first and second light colored films 52, 54 and dark colored film 56. Desirably, the first and second light colored films comprise white, substantially opaque stress-whitened microporous films such as those described herein above. The first and second film layers 52, 54 can have a combined thickness (in the non-embossed regions) between about 5 $\mu$m and about 35 $\mu$m and more desirably between about 7 $\mu$m and about 20 $\mu$m. Darker colored layer 56, that is darker with relation to that of layers 52 and 54, can have a thickness (in the non-embossed regions) of between about 3 $\mu$m and about 30 $\mu$m and more desirably between about 7 $\mu$m and about 20 $\mu$m. Desirably, the multilayer film has a total thickness of between about 12 $\mu$m and about 35 $\mu$m (in the non-embossed regions) and more desirably between about 15 $\mu$m and about 25 $\mu$m. First sheet 57 can comprise a diaphanous sheet such as, for example, a low basis weight nonwoven web. Second sheet 58 can comprise a substantially opaque sheet such as for example a nonwoven web with good opacity or coverage. As an example, the second nonwoven sheet can comprise a meltblown fiber web, a spunbond fiber web or spunbond/meltblown laminates. As a particular example, the second sheet can comprise a 5 to 20 g/m$^2$ meltblown fiber web. By way of example only, suitable meltblown fiber webs and laminates thereof are disclosed in U.S. Pat. No. 3,849,241 to Butin et al.; U.S. Pat. No. 5,160,746 to Dodge et al.; U.S. Pat. No. 5,271,883 to Timmons et al. and U.S. Pat. No. 4,041,203 to Brock et al. By employing an opaque sheet proximate the second side of the multilayer film 51, it is possible to provide a multilayer structure having a first side exhibiting a color-contrasted pattern achieved by translucent regions 60 which contrast with the non-embossed regions of the first light colored layer 52 and a second or opposite side having a more uniform and/or substantially uniform appearance. It is noted that the second sheet is desirably co-extensive with the multilayer film 51 and can be either affixed to the multilayered film as an integral part of the laminate or can be a separate, unattached layer.

In a further aspect of the present invention, embossed multilayer films can have improved masking properties while providing a film with a substantially uniform outward appearance. The outer microporous film can comprise a light color, e.g. white, and an inner microporous film can comprise a film have pale color. In this regard, as indicated above, the intensity or brightness of color within a film is reduced when stretched to become microporous. By utilizing a film with low levels of colorants, once rendered microporous the film exhibits a pale or "washed-out" color that is off-white in nature. Once embossed, the embossed regions become translucent and contrast with the unembossed regions, however there is little or no discernable color contrast within these regions thereby providing a multilayer film with a substantially uniform color. However, while the low level of pigments within the inner film help mask or neutralize colors within the interior of the absorbent article. As an example, the inner film can have low levels of pigments that give the inner film a light purple or violet color and the outer film can comprise a white film. Once stretched the inner film takes on off-white appearance having a subtle purple hue. Due to the low colorant loadings the embossed film retains a substantially uniformly white appearance. However, this film provides improved urine masking properties relative to white films without this additional pigment. As indicated above, the masking or neutralizing colors can be selected to neutralize or mask other colors as desired.

Absorbent articles, such as personal care articles, generally include a liquid permeable topsheet, which faces the wearer, and a liquid-impermeable bottom sheet or outer cover. Disposed between the topsheet and outer cover is an absorbent core, often the topsheet and outer cover are sealed to encase the absorbent core. Although the following detailed description will be made in the context of a disposable diaper, one skilled in the art will appreciate that the concepts of the present invention would also be suitable for use in connection with other types of absorbent articles, particularly other personal care products. In addition, although the present invention is described in the context of several specific configurations, it will be appreciated that further combinations or alterations of the specific configurations discussed below may be made by one skilled in the art without departing from the spirit and scope of the present invention.

Figure 5:
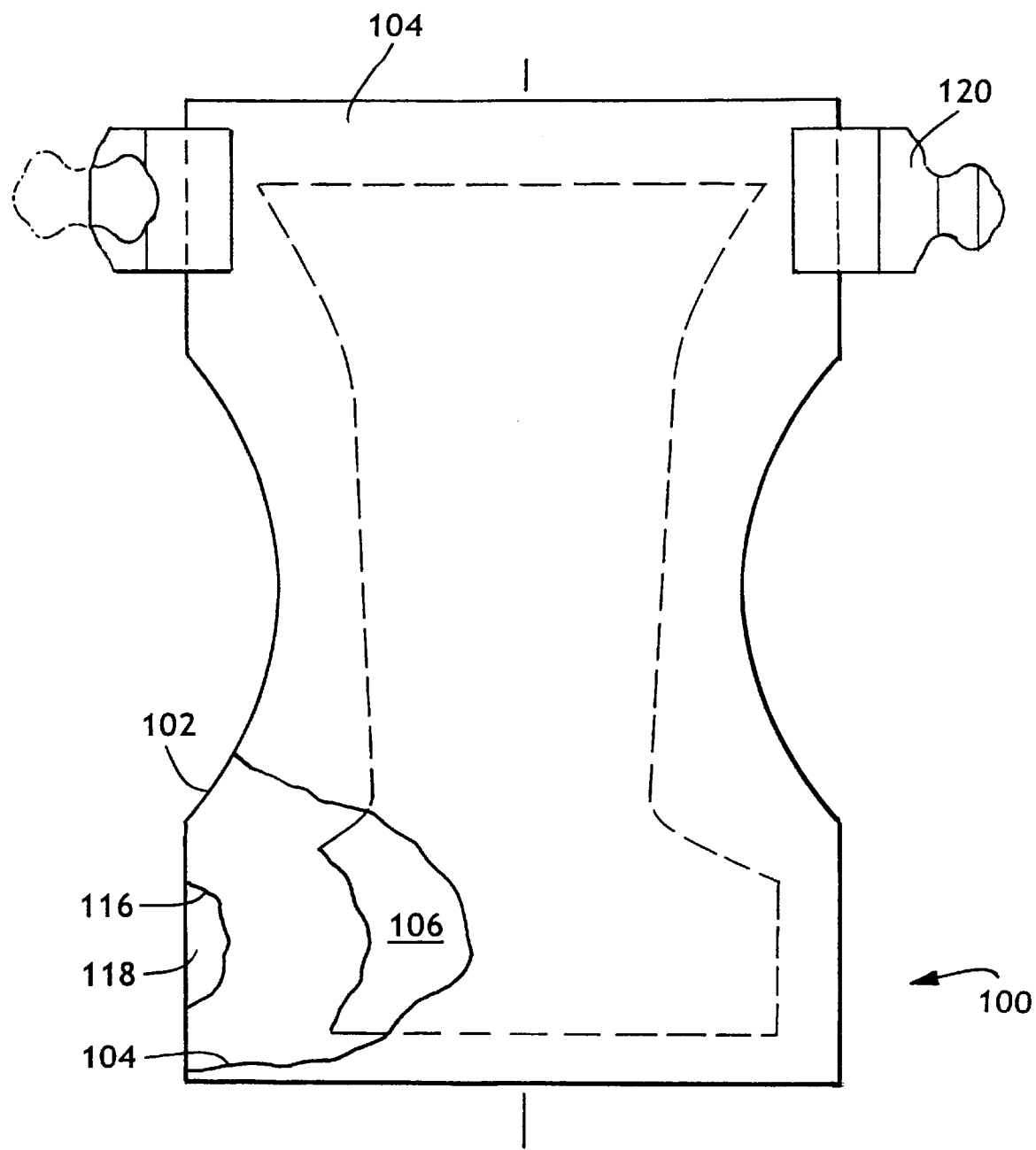
FIG. 5 is a partially broken-away perspective view of a diaper in a flat, uncontracted state.

In reference to FIG. 5, diaper 100 can comprise a liquid-impervious breathable outer cover 102, a liquid permeable topsheet 104 positioned in facing relation to the outer cover 102, and an absorbent core 106 between the outer cover 102 and topsheet 104. The diaper 100 may be of various shapes such as, for example, an overall rectangular shape, T-shape or an hourglass shape. The topsheet 104 is generally coextensive with the outer cover 102 but may optionally cover an area that is larger or smaller than the area of the outer cover 102, as desired. Portions of the diaper 100, such as a marginal section of the outer cover 102, may extend past the terminal edges of the absorbent core 106. In the illustrated embodiment, for example, the outer cover 102 can extend outwardly beyond the terminal marginal edges of the absorbent core 106 to form side margins and end margins of the diaper 100.

The topsheet 104 preferably presents a body-facing surface that is compliant, soft to the touch, and non-irritating to the wearer's skin. The topsheet 104 is suitably employed to help isolate the wearer's skin from liquids held in the absorbent core 106. In order to present a dryer surface to the wearer, the topsheet 104 may be less hydrophilic than the absorbent core 106 and also sufficiently porous to be readily liquid permeable. Topsheets are well known in the art and may be manufactured from a wide variety of materials, such as porous foams, reticulated foams, apertured plastic films, natural fibers (i.e., wool or cotton fibers), synthetic fibers (i.e., polyester, polypropylene, polyethylene, etc.), or a combination of natural and synthetic fibers. For example, the topsheet can comprise a spunbond fiber web of polyolefin fibers or a bonded-carded web composed of natural and/or synthetic fibers. In this regard the topsheet may be composed of substantially hydrophobic material treated with a surfactant or otherwise processed to impart the desired level of wettability and liquid permeability.

The baffle or outer cover 102 may comprise a breathable liquid-impervious structure and can comprise the multilayer films and/or laminates thereof of the present invention. In the particular embodiment shown in FIG. 5, the outer cover comprises a breathable liquid impervious multilayer film 116 (shown in FIG. 5 as a single layer) and one or more additional nonwoven layers 118. In this regard, the embossed films described herein are well suited to functioning as an outer cover in diapers and other personal care articles. When utilizing patterned films in which the pattern is visible substantially on only one side, the side having the visible contrasting pattern will face outwardly and the side having substantially no visible pattern or a less distinct pattern will face the interior of the absorbent article.

Between the breathable liquid-impervious outer cover 102 and the liquid pervious topsheet 104 is positioned an absorbent core 106 which typically includes one or more absorbent materials such as, for example, superabsorbent particles, wood pulp fluff fibers, synthetic wood pulp fibers, synthetic fibers and combinations thereof. Wood pulp fluff, however, commonly lacks sufficient integrity alone and has a tendency to collapse when wet. Thus, it is often advantageous to add a stiffer reinforcing fiber such as polyolefin meltblown fibers or shorter length staple fibers, typically provided as a coform material as described, for example, in U.S. Pat. No. 4,818,464 to Lau and U.S. Pat. No. 4,100,324 to Anderson et al. To improve the integrity of the absorbent core and/or liquid distribution of the same, the absorbent core 106 can employ a hydrophilic tissue wrapsheet (not shown in FIG. 5) as desired. The absorbent core may have any of a number of shapes, the size of which will vary with the desired loading capacity, the intended use of the absorbent article and other factors known to those skilled in the art. The various components of the diaper can be integrally assembled together employing various means of attachment known to those skilled in the art such as, for example, adhesive bonding, ultrasonic bonds, thermal bonds or combinations thereof.

In addition, diaper 100 can further include a pair of fasteners 120 which are employed to secure the diaper 100 about the waist of the wearer (not shown). Suitable fasteners include hook-and-loop type fasteners, adhesive tape fasteners, buttons, snaps, mushroom-and-loop fasteners and the like. However, one skilled in the art will recognize that numerous additional components may be integrally incorporated within a diaper or personal care article without departing from the spirit of the present invention. For example, it is common for diapers to include elasticized leg bands (not shown) which help secure the diaper to the wearer and, thus, help reduce leakage from the diaper. Similarly, it is also known to include a pair of elasticized, longitudinally extending containment flaps (not shown which are configured to maintain a substantially upright, perpendicular arrangement along the central portion of the diaper to serve as an additional barrier to the lateral flow of body exudates. Further, it is also common to include a surge management layer positioned between the topsheet 104 and the absorbent core 106 in order to help prevent pooling of fluids on the portion of the diaper adjacent the wearer's skin.

These and other components are well known and the manner and method of using the same in connection with the absorbent article of the present invention will likewise be readily appreciated by those skilled in the art.

In addition to personal care articles, the present invention can be used a variety of other applications including, but not limited to, garments, infection control products and protective covers. As further specific examples, the distinctly patterned films and laminates of the present invention can be used in wipes such as, for example, infant care wipes, industrial wipers, hand wipes and so forth. The multilayered films and laminates of the present invention are likewise suitable for use in numerous other applications.

Tests

Hunter Color Numbers: The Hunter Color numbers were obtained using a HUNTERLAB Color Difference Meter model no. D25 DP-9000 (available from Hunter Associates Laboratory of Reston, Va.) and in accord with the manufacturers instruction manual (manual version 1.6 dated July 1994). The resulting values are reported in CIE L*a*b* units.

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a better barrier to liquid penetration than a fabric with a lower hydrohead does. The hydrohead data cited herein was obtained in accord with Federal Test Standard 191A, Method 5514 except modified as noted below. The hydrohead was determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent to clamps is ignored.) Unsupported materials, such as a thin film, are supported to prevent premature rupture of the specimen.

WVTR: The water vapor transmission rate (WVTR) for the sample materials was calculated in accordance with ASTM Standard E96-80. Circular samples measuring three inches in diameter were cut from each of the test materials and a control which was a piece of CELGARD 2500 film from Hoechst Celanese Corporation of Sommerville, N.J. CELGARD 2500 film is a microporous polypropylene film. Three samples were prepared for each material. The test cups were number 68-1 Vapometer cups distributed by Thwing-Albert Instrument Company of Philadelphia, Pa. One hundred milliliters of water were poured into each vapometer cup and individual samples of the test materials and control material were placed across the open tops of the individual pans. The vapometer cups were mechanically sealed along the edges of the cup, leaving the associated test material or control material exposed to the ambient atmosphere over a 6.8 centimeter diameter circle having an exposed area of approximately 33.17 square centimeters. The cups were placed in a convection type oven at 100° F. (37.7° C.) for 24 hours. The oven was a constant temperature oven with external air circulating through it to prevent water vapor accumulation inside. After 24 hours, the pans were removed from the oven and weighed again. The preliminary test water vapor transmission rate values were calculated with Equation (I) below:

$$\text{Test } WVTR = (\text{grams weight loss over 24 hours}) \times 315.5 \text{ g/m}^2/24 \text{ hours} \quad (I)$$

The relative humidity within the oven was not specifically controlled. Under the predetermined set conditions of 100° F. (37.7° C.) and ambient relative humidity, the WVTR for the CELGARD 2500 control has been defined to be 5000 grams per square meter for 24 hours. Accordingly, the control sample was run with each test and the preliminary test values were corrected to set conditions using Equation (II) below:

$$\text{Standardized } WVTR = (\text{Test } WVTR/\text{control } WVTR) \times (5000 \text{ g/m}^2/24 \text{ hours}) \quad (II)$$

EXAMPLES

Example 1

A two-layer, co-extruded, filled-film with a first layer and a color-pigmented second layer was produced using the cast film process. The first layer comprised 50% of the film thickness and had the following composition: 65% by weight filler compounded with 34.8% by weight of a propylene copolymer (CATALLOY KS-357, 0.88 g/cc, 30 Ml, available from Montel North America Inc. of Wilmington, Del.), and 0.2% thermo-oxidative stabilizer. The second layer also comprised 50% of the two-layer film thickness and had the following composition: about 60% by weight filler compounded with about 19.9% by weight of linear low density polyethylene (DOWLEX 2035, 0.919 g/cc, 6 Ml, available from Dow Chemical Co. of Midland, Mich.) and about 19.9% by weight of linear low density polyethylene (AFFINITY PT-1409, 0.911 g/cc, 6 Ml, available from Dow Chemical Co. of Midland, Mich.), and about 0.2 weight % thermo-oxidative stabilizer. The second layer was extruded with a resin concentrate (SCC-18688 Red Shade Blue available from Standbridge Color Corporation of Social Circle, Ga.) in which 3% of the concentrate was blue pigment (copper phthalocyanine of the alpha crystal form rendered solvent she, CAS Registry #147-14-8) dispersed in equal amount of polyethylene wax (AC16 available from Allied Signal of Morristown, N.J.), and the remainder of the concentrate was the blend of polymers and additives in the second layer formulation. The actual pigment loading in the second layer of the film was 0.030%. The filler used in both the first and second layers was a fatty acid coated, ground calcium carbonate with an average particle size of about 1 micrometer, available from ECC of America, Sylacauga, Ala.

The co-extruded film was approximately 38 $\mu$m (1.5 mils) thick with a basis weight of 65 grams per square meter (gsm). The film was then stretched in the machine direction to approximately 3.3 times its starting length on a machine direction orientor (MDO), such as equipment which is available, for example, from the Marshall and Williams Company of Providence, R.I., to induce stress-whitening and formation of micropores in the film. The resulting microporous film was breathable having a measured WVTR of about 2840 g/m$^2$/24 hours. The stress-whitening and micropore formation caused changes in the light scattering properties so that the film became a lighter tone of the original colors, the unpigmented first layer appeared white and the pigmented second layer appeared a paler tone of the original blue color. The stretched film was then laminated to a diaphanous 20 g/m$^2$ basis weight point-bonded spunbond, made of propylene copolymer (6D43 which is approximately 3% ethylene, available from Union Carbide Corp. of Danbury, Conn.). The spunbonded web was bonded to the first layer of the film. Lamination was achieved with a "Baby Objects" steel pattern roll (12% bond area, 102° C.) against a flat steel anvil roll (82° C.) with approximately 145 pli±15 pli (25.9±2.7 kg/cm). Because of the heat and pressure applied in the lamination process to the bond pattern areas, the pores collapsed in the microporous films and the bonded regions became translucent. However, the resulting laminate had a light background and intensified color (blue) in the lamination or patterned areas, resulting in a laminate with aesthetically pleasing, print-like patterns.

Example 2

A breathable filled film laminate was made with the same materials and process as described in Example 1, except in the co-extruded film, the first layer was 70% of the film thickness and the blue pigmented second layer was 30% of the film thickness. Because of the heat and pressure applied in the lamination process to the bond pattern areas, the pores collapsed in the film and the bonded regions became translucent. The resulting laminate had a light background and intensified color (blue) in the lamination or patterned areas, resulting in a laminate with aesthetically pleasing, print-like patterns.

Example 3

A breathable filled film laminate was made with the same materials and process as described in Example 1 except that the first layer contained only 61% by weight calcium carbonate and also contained 4% by weight $TiO_2$. Because of the heat and pressure applied in the lamination process to the bond pattern areas, the pores collapsed in the film and the bonded regions exhibited a contrast. The resulting laminate had a light background and blue color in the lamination or patterned areas, resulting in a laminate with print-like patterns.

Example 4

A breathable filled film laminate was made with the same materials and process as described in Example 1 except that the second layer utilized a different pigment. The second layer had a purple color achieved by adding two pigments to the film: SCC-18688 Red Shade Blue and SCC-18689 Quinn Violet both available from Standbridge Color Corporation of Social Circle, Ga. The actual pigment loading in the base layer of the film was 0.030 weight % (25% by weight of the pigment was the blue pigment and the remaining 75% was the violet pigment).

The pigment, SCC-18688 Red Shade Blue, was provided in the form of a concentrate resin in which 3% of the concentrate resin was blue pigment (copper phthalocyanine of the alpha crystal form rendered solvent stable, CAS Registry #147-14-8) dispersed in an equal amount of polyethylene wax (Allied AC16), and the remainder of the concentrate was the blend of polymers and additives in the second layer formulation. The pigment, SCC-18689 Quinn Violet, was also provided in the form of a concentrate resin in which 3% of the concentrate resin was quinacridone violet pigment (cyclized 2,5-diarylaminoterephthalic acid or oxidized dihydroquinacridone, CAS Registry #1047-16-1) and the remainder of the concentrate resin was the blend of polymers and additives in the second layer formulation. Because of the heat and pressure applied in the lamination process to the bond pattern areas, the pores collapsed in the film and the bonded regions became translucent. The resulting laminate had a light background and intensified color (purple) in the lamination or patterned areas, resulting in a laminate with aesthetically pleasing, print-like patterns.

Example 5

A breathable filled film laminate was made with the same materials and process as described in Example 1 except that the second layer had a purple color, instead of blue, and comprised only 56.4% by weight calcium carbonate, 39.4% by weight polymer and also contained 4% by weight $TiO_2$. The purple color was achieved by adding two pigments to the base layer of the film, SCC-18688 Red Shade Blue and SCC-18689 Quinn Violet. The actual pigment loading in the second layer of the film was 0.050% (30% by weight of this was the blue pigment and 70% of this was the violet pigment). Because of the heat and pressure applied in the lamination process to the bond pattern areas, the pores collapsed in the film and the bonded regions became substantially darker. The resulting laminate had a light background and intensified color (purple) in the lamination or patterned areas, resulting in a laminate with aesthetically pleasing, print-like patterns.

In order to approximate the color of embossed regions within the multilayer films described above, the multilayer films were embossed across the entire fabric by running the multilayer film through a nip created by two heated flat calender rolls. The conditions were selected to approximate those experienced by the embossed regions of the above examples. The unstretched films, the unembossed stretched filled-films and the flat calendered films were evaluated for relative characteristics and the results are provided in Table I set forth below.

The data within Table I indicates that films of the present invention have good color-contrast. This is evidenced, in one aspect, by comparing the respective L* numbers for the stretched, uncalendered multilayer films with those of the stretched, calendered films (the stretched, calendered films being representative of the color of the embossed regions and the stretched, uncalendered multilayer films being representative of the color of the non-embossed regions). The stretched, calendered multilayer films have substantially lower L* numbers than those of the stretched, uncalendered films (lower L* numbers indicate a darker material). In addition, comparison of the a* and b* numbers for the respective stretched, uncalendered multilayer films and those for the stretched, calendered multilayer films also evidences that the color is substantially intensified when embossed. This allows formation of thin multilayer films having a light outer color since an underlying film can be provided with a color which varies regionally. More specifically, an underlying colored film can have intensely colored and/or dark embossed regions while simultaneously having less intensely colored or lighter colored non-embossed regions. The underlying film layer is thus only intensely colored or dark within the embossed regions. Such an underlying film structure allows the color of the thin non-embossed regions of the upper or overlying films to retain its true appearance without having an adulterated or darkened appearance such as caused by an intense or dark colored lower or underlying film. Thus, color-contrast is improved.

In addition, the data also shows that the color of the filled-films is lightened or muted upon stress-whitening as evidenced by comparing the respective Hunter numbers for the stretched, uncalendered films and the unstretched films. However, the color is intensified within the embossed regions as evidenced by comparing the respective. Hunter numbers for the stretched, uncalendered films and stretched, calendered films. In addition, the opacity values achieved for Examples 3 and 5 indicate that addition of titanium dioxide substantially increases the opacity of the multilayer films. Thus, when titanium dioxide is utilized within the colored layer, excellent opacity is achieved as well as good color contrast.

Example 6

A two-layer, co-extruded, filled-film with a first layer and a color-pigmented second layer was produced using the cast film process. The first layer comprised 25% of the film thickness and had the following composition: 70% (by weight) $CaCO_3$; about 20% polyethylene resins; and about 10% polyalphaolefin resin; and a minor amount of thermo-oxidative stabilizer. The second layer also comprised 75% of the two-layer film thickness and had the following composition: about 62% (by weight) $CaCO_3$ filler; about 38% polyethylene resins; about 3% violet color concentrate (30:70 mixture of SCC-18688 Red Shade Blue and SCC-18689 Quinn Violet both available from Standbridge Color Corporation of Social Circle, Ga.); about 6% $TiO_2$ concentrate (75% $TiO_2$ and about 25% polyethylene wax) and a minor amount of thermo-oxidative stabilizer.

The co-extruded film was approximately 38 μm (1.5 mils) thick with a basis weight of 65 grams per square meter (gsm). The film was then stretched in the machine direction to approximately 3.3 times its starting length on a machine direction orientor (MDO), such as equipment which is available, for example, from the Marshall and Williams Company of Providence, R.I., to induce stress-whitening and formation of micropores in the film. The resulting breathable microporous film caused changes in the light scattering properties so that the film became a lighter tone of the original colors, the unpigmented first layer appeared white and the pigmented second layer appeared a paler tone of the original violet color having an off-white appearance. The multilayer film was then laminated to a diaphanous 20 g/m² basis weight point-bonded spunbond, made of propylene copolymer. The spunbonded web was bonded to the first layer of the film. Lamination was achieved with a "Baby Objects" steel pattern roll (12% bond area, 102° C.) against a flat steel anvil roll (82° C.) with approximately 145 pli±15 pli (25.9±2.7 kg/cm). Because of the heat and pressure applied in the lamination process to the bond pattern areas, the pores collapsed in the microporous films and the bonded regions became translucent. However, when viewing the first or outer layer, the multilayer film laminate had a substantially uniform white, appearance. The bond points contrasted with the unbonded regions although there was no visibly distinct color contrast.

The film of Example 6 was compared to a control film which differed by having no violet pigment or $TiO_2$ within the second layer and instead employed additional polyethylene. The films were regionally embossed as described in Example 5 in order to evaluate the masking properties of the respective films. Each film was placed over a yellow substrate in order to evaluate the film's urine masking properties of the same. The Hunter Color measurements of the respective films are set forth in the table below.

TABLE 2

| Sample | Rd | A | B | Opacity |
| --- | --- | --- | --- | --- |
| Control | 76.8 | 1.8 | 4.9 | 76% |
| Example 6 | 80.1 | 0.9 | -0.2 | 90% |

Table 2 indicates that the multilayer film of Example 6 had Rd values (color lightness, light to dark) which were only slightly higher than those of the control film lacking any pigment and yet provided higher increases in overall film opacity. In addition, the control sample had a b* (yellow-blueness) value of 4.9 which indicates that yellow is visible through the multilayer film. However, while the film of Example 6 had color values a* (red-greenness) and b* that indicate significant red and blue components, the b* value of -0.2 indicates that the appearance of yellow was significantly reduced.

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the appended claims cover all such modifications, alterations and other changes.

TABLE 1

| | CIE L*a*b* units | | | | | | |
| --- | --- | --- | --- | --- | --- | --- | --- |
| EXAMPLE NO. | % LAYER A/% LAYER B | % $TiO_2$ IN LAYER A | % $TiO_2$ IN LAYER B | ACTUAL % PIGMENT IN LAYER B | STRETCH RATIO | CALENDERED | WVTR KC-CUP gram/m2/day |
| EXAMPLE 1 | 50%/50% | 0% | 0% | .030% blue | none | no | — |
|  | 50%/50% | 0% | 0% | .030% blue | 3.3x | no | 2839 |
|  | 50%/50% | 0% | 0% | .030% blue | 3.3x | yes | — |
| EXAMPLE 2 | 70%/30% | 0% | 0% | .030% blue | none | no | — |
|  | 70%/30% | 0% | 0% | .030% blue | 3.3x | no | 2481 |
|  | 70%/30% | 0% | 0% | .030% blue | 3.3x | yes | — |
| EXAMPLE 3 | 50%/50% | 4% | 0% | .030% blue | none | no | — |
|  | 50%/50% | 4% | 0% | .030% blue | 3.3x | no | 2679 |
|  | 50%/50% | 4% | 0% | .030% blue | 3.3x | yes | — |
| EXAMPLE 4 | 50%/50% | 0% | 0% | .030% (purple) | none | no | — |
|  | 50%/50% | 0% | 0% | .030% (purple) | 3.3x | no | 2902 |
|  | 50%/50% | 0% | 0% | .030% (purple) | 3.3x | yes | — |
| EXAMPLE 5 | 50%/50% | 0% | 4% | .050% (purple) | none | no | — |
|  | 50%/50% | 0% | 4% | .050% (purple) | 3.3x | no | 2829 |
|  | 50%/50% | 0% | 4% | .050% (purple) | 3.3x | yes | — |

TABLE 1-continued

| | | CIE L*a*b* units | | | | | | | |
|---|---|---|---|---|---|---|---|---|---|
| | % LAYER | HUNTER COLOR MEASUREMENTS | | | | | | | |
| EXAMPLE | A/% | L* | | a* | | b* | | Opacity | |
| NO. | LAYER B | Side A | Side B | Side A | Side B | Side A | Side B | Side A | Side B |
| EXAM-PLE 1 | 50%/50% | 74.85 | 75.14 | −9.83 | −9.82 | −21.49 | −21.42 | 53.17% | 53.58% |
| | 50%/50% | 92.58 | 90.06 | −3.00 | −5.16 | −6.92 | −10.68 | 89.71% | 88.02% |
| | 50%/50% | 73.86 | 73.24 | −10.45 | −10.47 | −23.26 | −23.23 | 34.28% | 33.16% |
| EXAM-PLE 2 | 70%/30% | 79.66 | 78.95 | −7.29 | −7.95 | −12.28 | −13.71 | 53.28% | 51.97% |
| | 70%/30% | 94.45 | 92.39 | −1.97 | −3.68 | −3.86 | −6.70 | 86.54% | 84.96% |
| | 70%/30% | 80.71 | 80.24 | −7.84 | −7.77 | −13.46 | −13.26 | 35.69% | 34.26% |
| EXAM-PLE 3 | 50%/50% | 85.47 | 79.62 | −5.784 | −9.67 | −12.02 | −19.92 | 77.38% | 71.37% |
| | 50%/50% | 93.15 | 90.62 | −3.22 | −5.328 | −7.35 | −11.11 | 89.81% | 88.01% |
| | 50%/50% | 78.01 | 76.68 | 3.22 | 3.61 | −15.68 | −16.57 | 59.87% | 58.26% |
| EXAM-PLE 4 | 50%/50% | 74.58 | 73.34 | 5.23 | 5.87 | −13.72 | −14.87 | 55.11% | 53.22% |
| | 50%/50% | 95.52 | 90.05 | 1.73 | 2.52 | −4.81 | −7.54 | 90.96% | 89.63% |
| | 50%/50% | 73.476 | 72.9 | 6.00 | 6.18 | −16.23 | −16.21 | 31.94% | 30.32% |
| EXAM-PLE 5 | 50%/50% | 76.85 | 75.55 | 3.28 | 3.87 | −15.71 | −17.81 | 78.02% | 76.78% |
| | 50%/50% | 91.19 | 88.69 | 1.28 | 1.74 | −6.12 | −9.17 | 92.75% | 91.63% |
| | 50%/50% | 76.90 | 77.52 | 3.28 | 3.17 | −16.62 | −15.91 | 58.13% | 59.26% |

L* color lightness, light to dark
a* red-greenness
b* Yellow-blueness

We claim:

1. A multilayer film comprising:
   a first microporous layer having a thickness less than about 30 micrometers and comprising (i) at least 35%, by weight, filler and (ii) polymer;
   a second microporous layer substantially continuously joined to said first layer, said second layer having a thickness less than about 30 micrometers and comprising (i) at least 35%, by weight, filler, (ii) polymer and (iii) a coloring agent;
   said multilayer film having a total basis weight less than about 45 g/m$^2$, a WVTR in excess of 500 g/m$^2$/24 hours and a hydrohead of at least 50 mbars and further wherein said multilayer film has embossed and non-embossed regions wherein the embossed regions color-contrast with said non-embossed regions.

2. The multilayer film of claim 1 wherein said second layer is darker than said first layer.

3. The multilayer film of claim 2 wherein the embossed regions of said first and second layer are translucent.

4. The multilayer film of claim 2 wherein the embossed regions of said first layer are translucent and the embossed regions of said second layer are substantially opaque.

5. The multilayer film of claim 4 wherein said second layer comprises between a positive amount and about 10% by weight titanium dioxide.

6. The multilayer film of claim 2 wherein said second layer is a two-toned film wherein the color is darker in said embossed regions relative to that in the non-embossed regions.

7. The multilayer film of claim 6 wherein said first and second layers each have a thickness less than about 15 micrometers and further wherein said multilayer film has a basis weight less than about 35 g/m$^2$.

8. The multilayer film of claim 7 wherein the non-embossed regions of said second layer have a Hunter Color Number L* above 70.

9. The multilayer film of claim 7 wherein non-embossed regions of the first layer comprise a white film.

10. The multilayer film of clam 9 wherein the color of said second layer is selected form the group consisting of purple, blue, pink, green, yellow and red.

11. The multilayer film of claim 2 wherein said multilayer film further comprises a third microporous layer substantially continuously joined to said second layer, said third layer having a thickness less than about 15 micrometers and comprising at least 45%, by weight, filler and polymer.

12. The multilayer film of claim 1 further comprising a diaphanous nonwoven web laminated to said multilayer film and proximate to said first layer.

13. An absorbent personal care article comprising:
    a liquid pervious topsheet;
    an absorbent core; and
    a liquid impervious outer cover, said outer cover comprising the multilayer film of claim 1.

14. The personal care article of claim 13 wherein said outer cover further comprises a diaphanous nonwoven fabric attached to the first layer of said multilayer film.

15. The personal care article of claim 14 wherein said multilayer film further comprises a third microporous layer and further wherein said second layer is positioned between said first and third layers.

16. The personal care article of claim 14 wherein said second layer is a two-toned film wherein the color is darker within said embossed regions relative to said non-embossed regions.

17. The personal care article of claim 16 wherein said first and second layers each have a thickness less than about 15 micrometers and further wherein said multilayer film has a basis weight less than about 35 g/m$^2$.

18. The personal care article of claim 16 wherein the non-embossed regions of said second layer have a Hunter Color Number L* above 70.

19. The personal care article of claim 16 further comprising a substantially opaque nonwoven sheet between said absorbent core and said outer cover.

20. The personal care article of claim 16 wherein said second layer comprises between about 0.5% by weight and about 10% by weight titanium dioxide.

21. The personal care article of claim 13 wherein the absorbent core of said personal care article takes upon a color of an absorbed liquid and wherein said coloring agent is a color that is the opposite color on a color wheel to the color of said absorbed liquid.

22. The personal care article of claim 21 wherein said personal care article is a diaper and said coloring agent is violet.

23. The personal care article of claim 21 wherein said personal care article is a feminine care article and said coloring agent is green.

* * * * *